United States Patent
Brunnett et al.

(10) Patent No.: US 8,945,164 B2
(45) Date of Patent: Feb. 3, 2015

(54) GUARD DEVICE FOR SURGICAL CUTTING AND EVOKED POTENTIAL MONITORING SYSTEM

(75) Inventors: William Charles Brunnett, Jacksonville, FL (US); Kevin Lee McFarlin, Jacksonville, FL (US); Benjamin Morris Rubin, Jacksonville Beach, FL (US); Robert Vaccaro, Ponte Vedra Beach, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 978 days.

(21) Appl. No.: 11/760,530

(22) Filed: Jun. 8, 2007

(65) Prior Publication Data

US 2007/0239187 A1  Oct. 11, 2007

Related U.S. Application Data

(63) Continuation-in-part of application No. 11/260,503, filed on Oct. 27, 2005.

(51) Int. Cl.
*A61B 17/32* (2006.01)
*A61B 17/16* (2006.01)
(Continued)

(52) U.S. Cl.
CPC ....... *A61B 17/32002* (2013.01); *A61B 17/1622* (2013.01); *A61B 17/1633* (2013.01); *A61B 5/0488* (2013.01); *A61B 17/1624* (2013.01); *A61B 17/1628* (2013.01);
(Continued)

(58) Field of Classification Search
CPC .................. A61B 17/1633; A61B 2017/00022
USPC ................................................. 606/170, 172
See application file for complete search history.

(56) References Cited

U.S. PATENT DOCUMENTS

| | | | |
|---|---|---|---|
| 3,835,858 | A | 9/1974 | Hagen |
| 3,847,154 | A | 11/1974 | Nordin |

(Continued)

FOREIGN PATENT DOCUMENTS

| | | |
|---|---|---|
| WO | 2005/074831 A2 | 8/2005 |
| WO | 2006/086367 | 8/2006 |
| WO | 2007051143 A1 | 5/2007 |

OTHER PUBLICATIONS

Silverstein, Otolaryngology Head and Neck Surgery article entitled "Adaptor for Continuous Stimulation (SACS) with the WR-S8 Monitor-Stimulator"; Sep. 1990; 103(3); pp. 493-496.

(Continued)

*Primary Examiner* — Thomas McEvoy
*Assistant Examiner* — Julie A Szpira
(74) *Attorney, Agent, or Firm* — Dicke, Billig & Czaja, PLLC

(57) ABSTRACT

A guard for use with a surgical cutting system. The guard includes a housing and wiring. The housing defines a longitudinal passageway, and is configured for releasable attachment to an instrument handpiece. The wiring is coupled to the housing and includes an electrically conductive wire and an insulative material. The wire defines opposing, first and second ends, with the first end being positioned within the passageway. The insulative material covers the wire apart from the first end such that the first end of the wire is exposed within the passageway. The first end of the wire establishes an electrical connection with a cutting tool shank upon placement within the passageway.

25 Claims, 12 Drawing Sheets

(51) Int. Cl.
  *A61B 5/0488* (2006.01)
  *A61B 17/00* (2006.01)
  *A61B 19/00* (2006.01)

(52) U.S. Cl.
  CPC .............. *A61B 2017/00022* (2013.01); *A61B 2017/00477* (2013.01); *A61B 2017/320032* (2013.01); *A61B 2019/481* (2013.01); *A61B 2217/005* (2013.01); *A61B 2217/007* (2013.01)
  USPC ...................................................... 606/172

(56) References Cited

U.S. PATENT DOCUMENTS

| | | | | |
|---|---|---|---|---|
| 4,655,215 | A * | 4/1987 | Pike | 606/42 |
| 4,941,472 | A * | 7/1990 | Moden et al. | 607/33 |
| 4,962,766 | A | 10/1990 | Herzon | |
| 5,013,317 | A * | 5/1991 | Cole et al. | 606/96 |
| 5,257,990 | A * | 11/1993 | Nash | 606/45 |
| 5,284,153 | A | 2/1994 | Raymond et al. | |
| 5,284,154 | A | 2/1994 | Raymond et al. | |
| 5,383,876 | A | 1/1995 | Nardella | |
| 5,474,558 | A | 12/1995 | Neubardt | |
| 5,584,843 | A | 12/1996 | Wulfman et al. | |
| 5,704,352 | A * | 1/1998 | Tremblay et al. | 600/300 |
| 5,891,094 | A * | 4/1999 | Masterson et al. | 604/113 |
| 5,928,158 | A * | 7/1999 | Aristides | 600/547 |
| 6,139,545 | A | 10/2000 | Utley et al. | |
| 6,298,256 | B1 | 10/2001 | Meyer | |
| 6,312,392 | B1 | 11/2001 | Herzon | |
| 6,423,070 | B1 | 7/2002 | Zeppelin | |
| 6,466,817 | B1 | 10/2002 | Kaula et al. | |
| 6,523,070 | B1 | 2/2003 | Stapleton et al. | |
| 7,066,940 | B2 * | 6/2006 | Riedel et al. | 606/79 |
| 7,101,370 | B2 * | 9/2006 | Garito et al. | 606/41 |
| 2002/0161372 | A1 | 10/2002 | Bolger et al. | |
| 2004/0022602 | A1 | 2/2004 | Singh et al. | |
| 2004/0122482 | A1 | 6/2004 | Tung et al. | |
| 2004/0260357 | A1 | 12/2004 | Vaughan et al. | |
| 2004/0260358 | A1 | 12/2004 | Vaughan et al. | |
| 2005/0033282 | A1 * | 2/2005 | Hooven | 606/41 |
| 2005/0096649 | A1 | 5/2005 | Adams | |
| 2005/0137453 | A1 * | 6/2005 | Ouchi et al. | 600/106 |
| 2007/0100334 | A1 | 5/2007 | McFarlin et al. | |

OTHER PUBLICATIONS

I. San, Turk Otolarengoloji article entitled "Continuous Stimulation Monitoring of the Facial Nerve"; Feb. 2001; pp. 251-254.
Silverstein; Silverstein Institute Ear Research Publication Summaries article entitled "Routine Identification of the Facial Nerve Using Electrical Stimulation During Otological and Neurotological Surgery"; www.silversteininstitute.com; Dec. 2005; 1 pg.

* cited by examiner

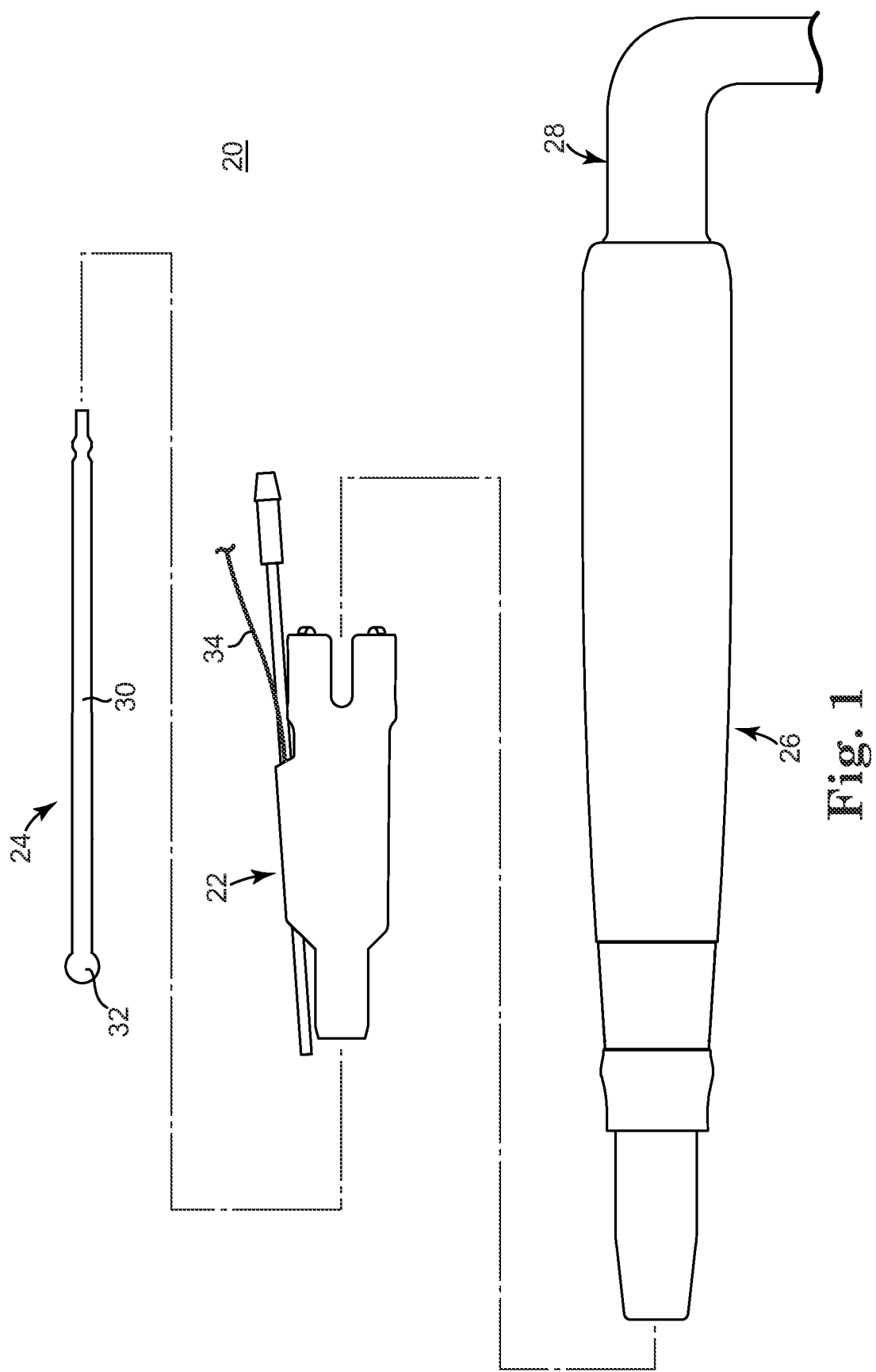

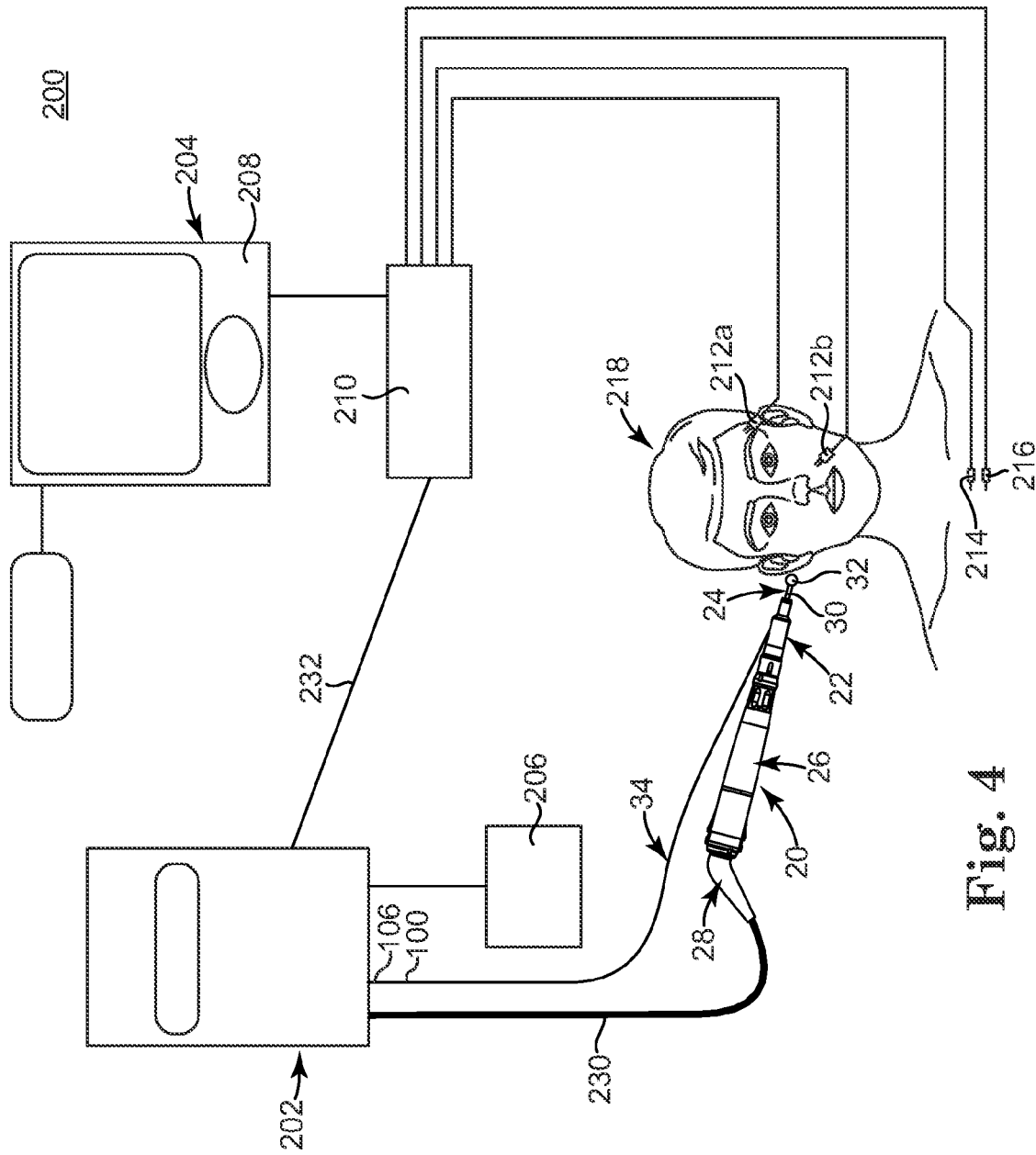

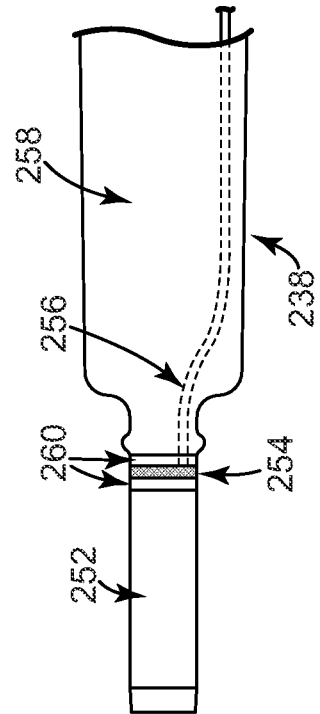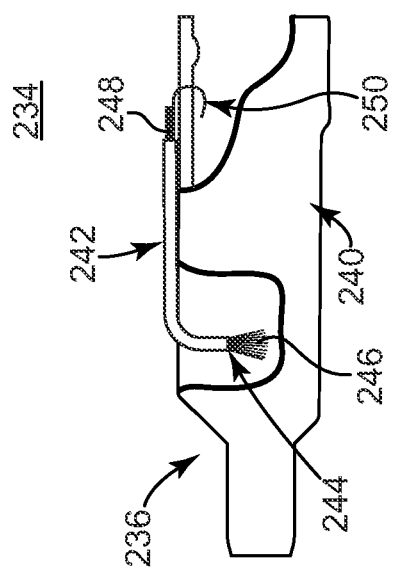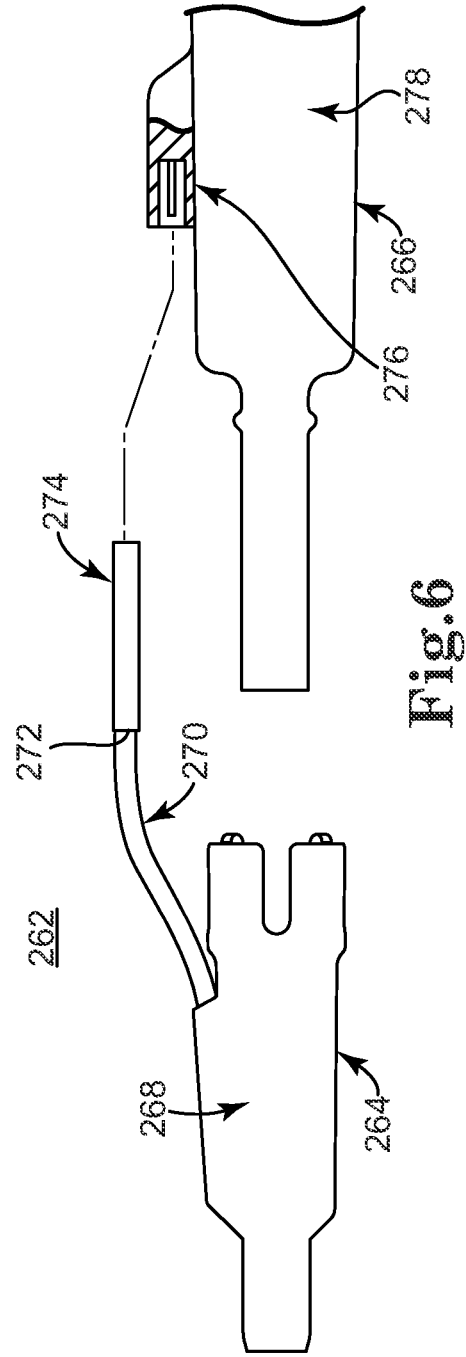

GUARD DEVICE FOR SURGICAL CUTTING AND EVOKED POTENTIAL MONITORING SYSTEM

CROSS REFERENCE TO RELATED APPLICATIONS

This application is a continuation-in-part of U.S. application Ser. No. 11/260,503, filed Oct. 27, 2005, and entitled "Instrument and System for Surgical Cutting and Evoked Potential Monitoring," the teachings of which are incorporated herein by reference.

BACKGROUND

The present disclosure relates to surgical cutting and surgical cutting instruments and systems. More particularly, aspects relate to surgical cutting instruments and systems capable of both high-speed cutting and electrical probing or evoked potential monitoring functions, as well as components useful with such systems.

Surgical micro-cutting instruments employing an elongated cutting tool having a cutting tip (e.g., a bur) at a distal end thereof are well-accepted for use in various surgical cutting procedures, for example those where access to the surgical site is gained via a narrow portal or passage. The cutting tool is rotatably driven by a motor to effectuate a desired cutting procedure, and a handpiece effectuates and maintains coupling of the cutting tool with the motor. The cutting tool may be supported solely by the handpiece, or may be disposed within an outer tube for additional support.

Micro-cutting procedures (e.g., ENT) typically entail removing tissue, bone, etc., from bodily areas that are otherwise in close proximity to nerves or other delicate bodily structures. Thus, a danger exists of potentially severing or otherwise damaging nerves (or other structures) through inadvertent cutting or excessive heat. As such, conventional micro-cutting procedures oftentimes require additional steps and instruments for estimating nerve location(s) to safely complete the procedure. For example, evoked potential monitoring devices can be employed to periodically evaluate location of the cutting tip relative to nerves via patient response to an applied stimulating energy. While carrying out such procedures, a surgeon may be required to sequentially remove tissue/bone with the micro-cutting instrument and then probe a cut area for nerves (or other bodily structure) using a separate implement otherwise provided with the evoked potential monitoring device. This is clearly time-consuming and thus undesirable. More recently, systems have been proposed in which the cutting instrument provides both cutting and electrical stimulation (in connection with evoked potential monitoring) as described, for example, in commonly-owed U.S. Publication No. 2007/0100378. Any improvements in such constructions would be well-received.

SUMMARY

Some aspects in accordance with principles of the present disclosure relate to a guard for use with a surgical cutting system. The guard includes a housing and wiring. The housing defines a leading end, a trailing end, and a longitudinal passageway extending therebetween. In this regard, the passageway is open at a trailing end opening that is otherwise sized to releasably receive a surgical cutting instrument handpiece, and is also open at a leading end opening sized to releasably receive a cutting tool shank. The wiring is coupled to the housing and includes an electrically conductive wire and an electrically non-conductive insulative material. The wire defines opposing, first and second ends, with the first end being positioned within the passageway. The insulative material covers at least a majority of the wire apart from the first end such that the first end of the wire is exposed within the passageway. With this construction, the first end of the wire establishes an electrical connection with a cutting tool shank upon placement within the passageway. The second end of the wire can be electrically coupled, directly or indirectly, to a separate energy source. The wire thus facilitates delivery of stimulating energy to the surgical site via contact with the cutting tool shank. In some embodiments, the first end of the wire includes a plurality of wire strands forming a wire brush-type construction.

Other aspects in accordance with principles of the present disclosure relate to a surgical cutting system including a cutting tool, a motor assembly, a handpiece, and a guard. The cutting tool includes a cutting tip and a tool shank. The motor assembly includes a motor rotatably driving a drive mechanism. The handpiece maintains the motor assembly and is configured to facilitate selective connection of the tool shank with the drive mechanism within a bore defined by the handpiece. Finally, the guard includes a housing and wiring coupled thereto. The housing defines a leading end, a trailing end, and a longitudinal passageway extending therebetween. The trailing end is configured for releasable attachment to the handpiece via a trailing end opening of the passageway. Further, the leading end is configured to permit selective placement of the tool shank within the passageway via a leading end opening. The wiring includes an electrically conductive wire and an electrically non-conductive insulative material. The wire defines opposing, first and second ends. The first end is positioned within the passageway. The insulative material encompasses at least a majority of the wire apart from the first end such that the first end is exposed within the passageway. With this construction, upon final assembly, the handpiece is disposed within the passageway. The tool shank extends through the passageway and into the bore, and is connected to the drive mechanism. Finally, the first end of the wire contacts the tool shank. As such, an electrical pathway is established from the second end of the wire to the cutting tip. Where desired, the guard can be removed from attachment with the handpiece. In some embodiments, the system further includes an evoked potential monitoring system having an energy source that is selectively electrically coupled to the second end of the wire. With these alternative constructions, the energy source applies a stimulating energy to the cutting tip via the wire, and the contact between the first end of the wire and the tool shank. In yet other embodiments, the handpiece includes an outer housing and is configured to electrically isolate the cutting tool from the outer housing.

Yet other aspects in accordance with principles of the present disclosure relate to a method of performing a surgical cutting procedure. The method includes providing a handpiece defining a proximal side, a distal side, and a central bore. A guard is also provided and includes a housing and wiring. The housing defines a longitudinal passageway extending between, and open at, a trailing end opening, and a leading end opening. The wire is coupled to the housing, and includes a first end positioned within the passageway. Further, an electrically non-conductive insulative material covers at least a majority of the wire apart from the first end such that the first end of the wire is exposed within the passageway. The guard housing is assembled to the distal side of the handpiece such that the passageway is open to the bore. A tool shank of a cutting tool is extended within the leading end of the passageway and into the bore such that a cutting tip of the cutting tool is positioned distal the guard. Further, upon insertion, the first end of the wire contacts the tool shank. The tool shank is also mounted to a drive mechanism of a motor assembly otherwise maintained by the handpiece. An evoked potential monitoring system is electrically connected to the second end of the wire such that an energy source of the evoked potential monitoring system is in electrically communication with the cutting tip. The cutting tip is then delivered to a surgical site. The motor assembly is operated to perform a cutting operation with the cutting tip at the surgical site. A stimulation energy is applied to the cutting tip via the energy source, and a proximity of the cutting tip to a nerve is detected based upon reference to the stimulation energy, such as EMG response.

BRIEF DESCRIPTION OF THE DRAWINGS

FIG. 1 is an exploded view of a surgical cutting instrument including a guard in accordance with aspects of the present disclosure;

FIG. 4 is a block diagram of a surgical cutting system, including the instrument of FIG. 1;

FIG. 5 is a simplified side view of another surgical cutting instrument in accordance with aspects of the present disclosure;

FIG. 6 is a simplified side view of another surgical cutting instrument in accordance with aspects of the present disclosure;

DETAILED DESCRIPTION

Figure 2A:
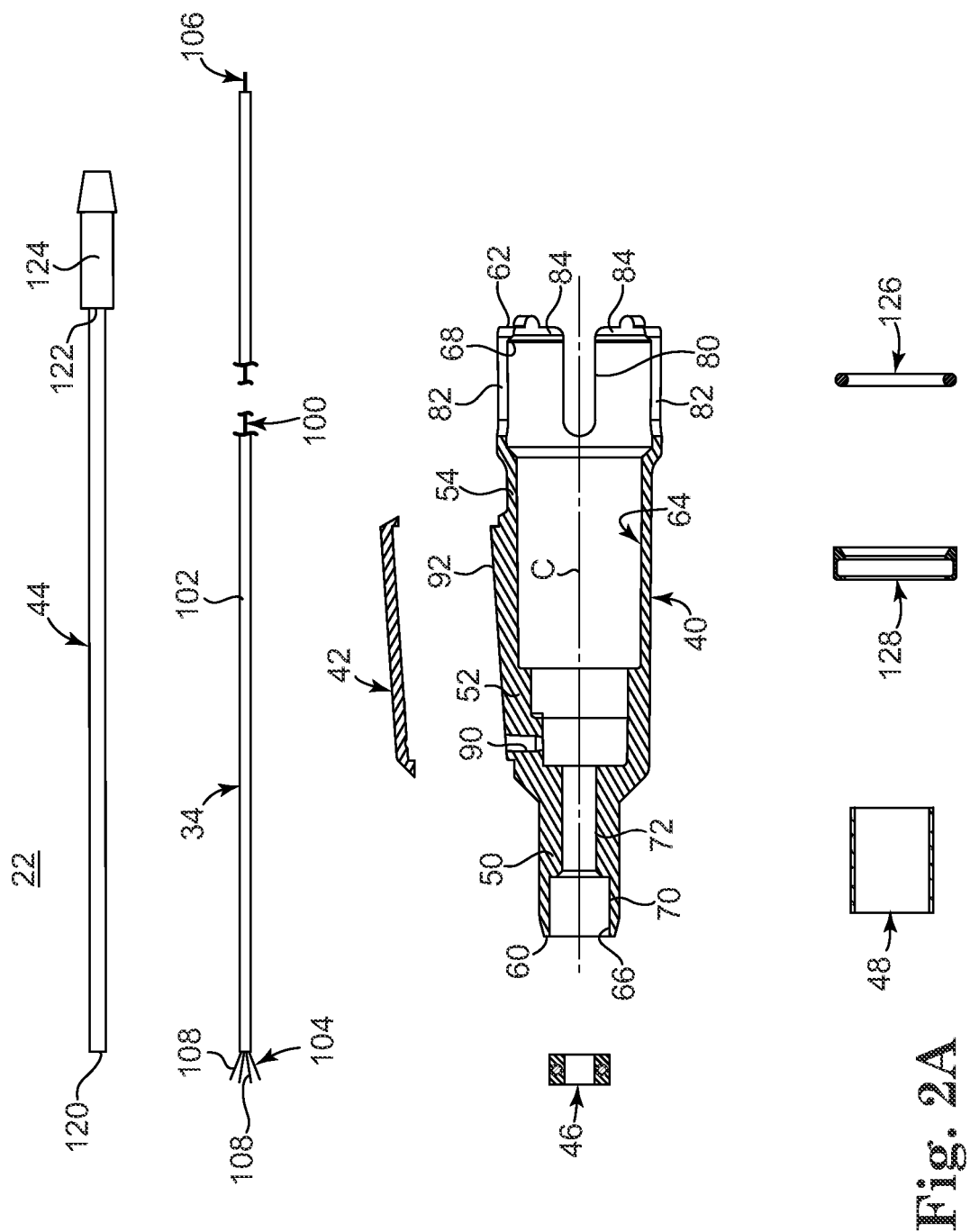
FIG. 2A is an exploded, cross-sectional view of the guard of FIG. 1.

A surgical cutting instrument 20 including a guard 22 in accordance with principles of the present disclosure is shown in FIG. 1. The instrument 20 includes the guard 22 along with a cutting tool 24 and a handpiece 26 maintaining a motor assembly 28 (referenced generally). Details on the various components are provided below. In general terms, however, the cutting tool 24 includes a tool shank 30 and a cutting tip 32. The guard 22 is releasably attached to the handpiece 26, and permits releasable connection of the tool shank 30 to the motor assembly 28 internally within the handpiece 26. Further, the guard 22 provides wiring 34. Upon assembly of the guard 22 to the handpiece 26, as well assembly of the cutting tool 24 to the handpiece 26/motor assembly 28, the wiring 34 establishes an electrical connection with the tool shank 30. During use, then, the wiring 34 delivers electrical energy from a source (not shown) to the cutting tip 32 via the internal, electrical connection between the tool shank 30 and the wiring 34. As such, the surgical instrument 20 is highly useful with various procedures in which cutting and electrical stimulation at the cutting tip 32 (e.g., evoked potential monitoring) is desired.

Figure 2B:
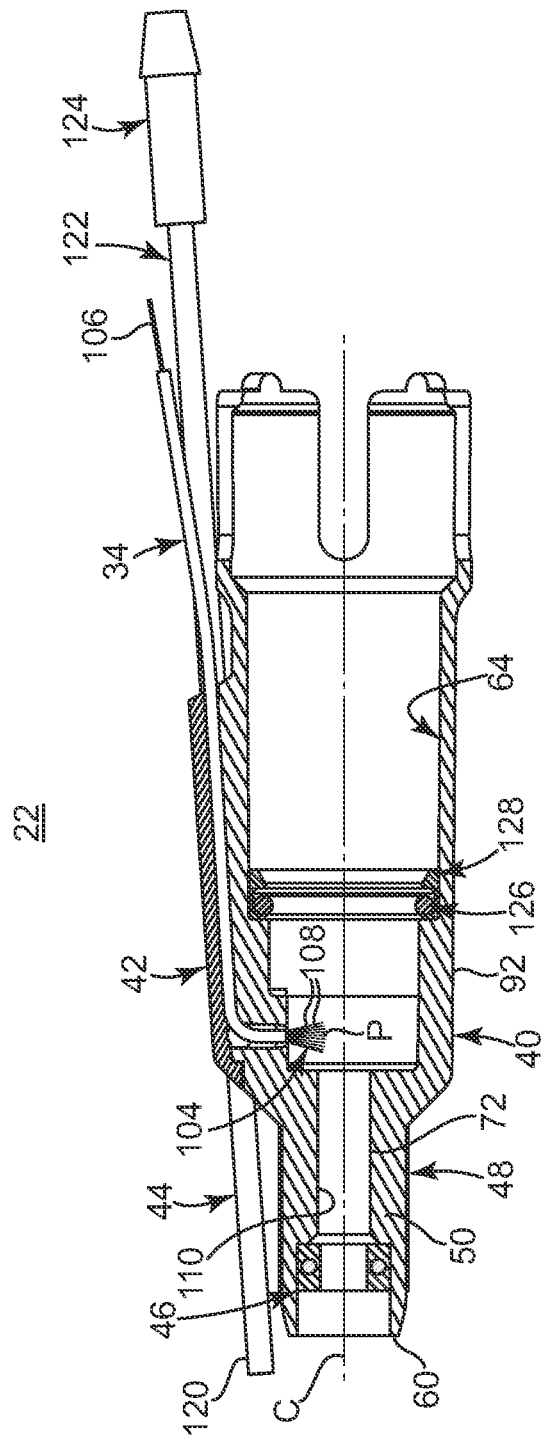
FIG. 2B illustrates the guard of FIG. 2A upon final assembly.

The guard 22 is shown in greater detail in FIGS. 2A and 2B. In addition to the wiring 34, the guard 22 includes a housing 40, an optional cover plate 42, optional irrigating tubing 44, an optional bearing member 46, and an optional collar 48. In general terms, the wiring 34 is affixed to the housing 40, for example via the cover plate 42. In this regard, an end of the wiring 34 is exposed within an interior of the housing 40, as described in greater detail below. The irrigation tubing 44 is also affixed to the housing 40, and provides a conduit for delivery of liquid distal the housing 40. In other configurations, however, the irrigation tubing 44 can be eliminated. Where provided, the bearing member 46 rotationally supports the tool shank 30 (FIG. 1) during use, and the collar 48 reinforces the bearing member 46/tool shank 30 interface.

The housing 40 can assume a wide variety of forms. As shown in FIG. 2A, the housing 40 generally defines a leading segment 50, an intermediate segment 52 and a trailing segment 54, it being understood that the segments 50-54 can be integrally formed such that the housing 40 is a homogeneous structure. Regardless, the leading segment 50 terminates at a leading end 60, the trailing segment 54 terminates at a trailing end 62, and the housing 40 forms a longitudinal passageway 64 extending between the ends 60, 62. The passageway 64 is open at the leading end 60 via a leading end opening 66; further, the passageway 64 is open at the trailing end 62 via a trailing end opening 68. With these designations in mind, the passageway 64 is sized at the leading end opening 66 to permit sliding insertion and removal of the cutting tool 24 (FIG. 1). For example, in some configurations, the passageway 64 is defined along the leading segment 50 as having a first portion 70 and a second portion 72. The first portion 70 is sized to receive (e.g., frictionally receive and maintain) the bearing member 46 (where provided), whereas the second portion 72 is sized to more closely match a diameter of the tool shank 30 (FIG. 1). Thus, a minimum effective diameter of the passageway 64 is defined along the second portion 72, as is a central axis C. The minimum effective diameter of the passageway 64 may further be reduced or defined by other regions of the housing 40 and/or by other components (apart from the cutting tool 24) assembled thereto. For example, the bearing member 46 can have an inner diameter smaller than that of the second portion 72, such that the bearing member 46 defines the minimum effective diameter of the passageway 64. In more general terms, then, the minimum effective diameter of the passageway 64 is defined by the surface(s) provided to directly support the cutting tool 24 upon insertion into the housing 40.

The trailing segment 54 is sized for releasable attachment or coupling to the handpiece 26 (FIG. 1) via the trialing end opening 68. For example, the trailing segment 54 can form one or more longitudinal slots 80 that collectively define two or more fingers 82. The fingers 82 are deflectable relative to the central axis C (e.g., radially outwardly). A relatively rigid construction of the housing 40 in some configurations imparts a biasing attribute to the fingers 82, such that when the fingers 82 are forced to deflect outwardly, the inherent bias causes the fingers 82 to self-transition back to the orientation of FIG. 2A. Regardless, the fingers 82 each terminate at a radial latch 84. As described below, the deflectable nature of the fingers 82 permits assembly of the housing 40 over the handpiece 26, with the latches 84 selectively engaging a corresponding feature of the handpiece 26. Alternatively, however, a wide variety of other constructions capable of effectuating releasable attachment of the housing 40 to the handpiece 26 are also acceptable.

Regardless of the manner in which the housing 40 is releasably attached to the handpiece 26 (FIG. 1), the passageway 64 has a size (e.g., diameter) commensurate with a corresponding dimension of the handpiece 26 at least along the trailing segment 54. Relative to the intermediate segment 52, the passageway 64 can have a diameter greater than the diameter along the leading segment 50 (e.g., the second portion 72 of the passageway 64). Regardless, the housing 40 further includes an aperture 90 extending through a thickness of the housing 40 at the intermediate segment 52, such that the aperture 90 is open to the passageway 64 as well as relative to an exterior 92 of the housing 40. As described in greater detail below, the aperture 90 is sized to receive or permit passage of a portion of the wiring 34, and maintains a desired position of the wiring 34 relative to the passageway 64.

The housing 40 can assume shapes differing from those reflected in the views of FIGS. 1 and 2A. With some constructions, however, the leading segment 50 has a reduced size (e.g., diameter) as compared to a remainder thereof to facilitate supporting of the tool shank 30 (FIG. 1) as described below. Regardless, the housing 40 is formed of an electrically non-conductive material, for example, a non-conductive plastic or ceramic material.

The wiring 34 includes a wire 100 and an electrically non-conductive insulative material 102. The wire 100 defines or extends between a first end 104 and a second end 106. As generally reflected in FIGS. 2A and 2B, the insulative material 102 is applied to the wire 100 so as to encompass (or electrically insulate) at least a majority of the wire 100. However, at least the first end 104 of the wire 100 is not covered by the insulative material 102, and thus is exposed. The second end 106 can also be exposed relative to the insulative material 102, or provided with or attached to an appropriate electrical connector (e.g., a socket connector) configured for electrical coupling with an appropriate energy source (not shown).

The wire 100 can be formed from one or more conventional electrical wiring materials, and can be a single length of wire or can be a plurality of individual wires bundled together. With some constructions, the wire 100 is a carbon fiber wire. Regardless of an exact material, the wire 100 can be formed such that at least at the exposed first end 104, the wire 100 provides a plurality of wire strands 108 that are splayed apart relative to one another. With this construction, the first end 104 assumes a brush-like configuration. For example, the wiring 34 can initially be provided as conventional electrical wiring (i.e., the wire 100 encompassed by the insulative material 102 along an entire length thereof), the insulative material 102 stripped from the first end 104, and the now-exposed strands 108 splayed apart. Alternatively, a variety of other constructions for the wiring 34 are also acceptable so long as the first end 104 of the wire 100 is electrically exposed.

With specific reference to FIG. 2B, upon final assembly of the guard 22, the wiring 34 is attached to the housing 40 such that the first end 104 of the wire 100 is positioned within the passageway 64 and the second end 106 is away from the housing 40. That is to say, upon final assembly, the second end 106 (and a segment of the wiring 34 adjacent the second end 106) is movable relative to the housing 40 and thus can easily be connected to a desired energy source. As a point of reference, the wiring 34 is reflected in FIG. 2B in shortened form, it being understood that a length of the wiring 34 can extend well beyond the housing 40. The cover plate 42 can be provided, and assists in securing the wiring 34 to the exterior 92 of the housing 40. For example, the wiring 34 can be assembled to the housing 40 such that the first end 104 is beyond the aperture 90 and within the passageway 64. A segment of the wiring 34 extending outwardly from the aperture 90 is placed against the housing exterior 92, and the cover plate 42 applied over the wiring 34. Where provided, the cover plate 42 is formed of an electrically non-conductive material (e.g., plastic) and is affixed to the housing 40 (e.g., ultrasonic welding) in securing the wiring 34. Alternatively, a variety of other manufacturing techniques can be employed to assemble the wiring 34 to the housing 40 that may or may not include the separate cover plate 42 (e.g., the wiring 34 can be insert-molded to the housing 40).

Regardless of the assembly technique, the wiring 34 is positioned such that the first end 104 of the wire 100 is positioned within the passageway 64. More particularly, the first end 104 is located so as to contact the cutting tool shank 30 (FIG. 1) upon insertion into the housing 40. For example, where the wire 100 is provided to include the splayed strands 108, at least some of the strands 108 extend in a radial fashion into the passageway 64, terminating at a point P in close proximity to the central axis C. More particularly, the termination point P of the first end 104 is radially spaced a distance from the central axis C that is less than the effective minimum diameter or radius of the passageway 64 (i.e., the diameter or radius defined by the bearing member 46, along the second portion 72, etc.). Thus, relative to the orientation of FIG. 2B, the termination point P of the wire end 104 extends "below" an upper wall surface 110 defined along the leading segment 50. With this configuration, intimate, physical contact between the wire end 104 and is ensured as the cutting tool shank 30 has a diameter commensurate with that of the bearing member 46 (with the one configuration of FIG. 2B); because the bearing member 46 effectively dictates a location of the tool shank 30 relative to the central axis C, contact with wire end 104 will consistently occur and be maintained.

With some configurations of the guard 22, the irrigation tubing 44 is provided. The irrigation tubing 44 can assume a variety of forms, and in some embodiments is formed of a relatively rigid material (e.g., stainless steel). Regardless, the irrigation tubing 44 extends between a distal end 120 and a proximal end 122. The proximal end 122 can be fluidly connected to or form a barb 124 of conventional design and otherwise adapted to facilitate fluid connection to tubing of a liquid source. As described in greater detail below, the irrigation tubing 44 is assembled to the housing 40 such that the distal end 120 is adjacent, preferably distally spaced from, the leading end 60 of the housing 40. In other embodiments, the irrigation tubing 44 can be eliminated.

Where provided, the optional bearing member 46 and collar 48 support the tool shank 30 (FIG. 1) during rotation thereof relative to the housing 40. Thus, the bearing member 46 defines an inner diameter commensurate with that of the tool shank 30, along with an appropriate rotational bearing surface. For example, the bearing member 46 can be a ball bearing-type assembly. Regardless, the bearing member 46 is preferably disposed and retained within the passageway 64 at or adjacent the leading end 60. The collar 48 serves to reinforce the bearing member 46, can prevent the bearing member 46 from "creeping" during use, and/or can prevent the housing 40 from cracking along the leading segment 50. Thus, the collar 48 can assume a variety of forms, and is assembled to the housing 40 in a region of the bearing member 46 (e.g., along an exterior of the leading segment 50). The collar 48 can be formed of a structurally rigid material, such as stainless steel. In other embodiments, one or both of the bearing member 46 and/or the collar 48 can be omitted.

In addition to the above, the guard 22 can include one or more other components. For example, an O-ring 126 or similar elastomeric body can be provided, maintained, or captured relative to the housing 40 by a holder 128. The holder 128 can be a separately formed component assembled to the housing 40 as shown, or can be integrally formed as part of the housing 40. As described below, the O-ring 126 provides vibrational dampening to the housing 40. Alternatively, the O-ring 126 can be omitted.

Figure 2C:
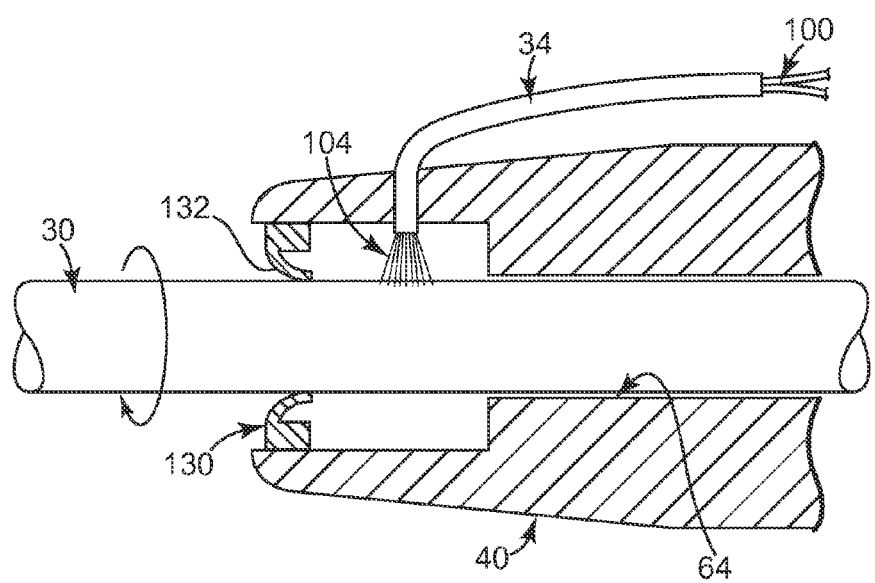
FIG. 2C is a simplified cross-sectional view of a portion of another guard in accordance with aspects the present disclosure.

As mentioned above, the guard 22 is shown in final, assembled form in FIG. 2B. Once again, the wiring 34 is affixed to the housing 40 such that the first end 104 is exposed at, and projects within, the passageway 64. Where provided, the irrigation tubing 44 is also affixed relative to the housing 40. For example, the irrigation tubing 44 can be molded within the cover plate 42, captured between the cover plate 42 and the housing 40, etc. As shown, the distal end 120 of the irrigation tubing 44 is adjacent or distally spaced from the leading end 60 of the housing 40. With this arrangement, liquid dispensed from the distal end 120 of the irrigation tubing 44 is less likely to enter the passageway 64. To further minimize opportunities for ingress of liquid (or other materials at the target site), the guard 22 can further include a lip seal 130 assembled to the housing 40 as shown in FIG. 2C. The lip seal 130 can be formed of a variety of materials, such as PTFE or other elastomer, and provides a deflectable flange 132 having a diameter smaller than that of the tool shank 30 (drawn generally). Upon assembly of the tool shank 30 within the passageway 64, then, the lip seal 130, and in particular the flange 132, seals against the tool shank 30. In other embodiments, the lip seal 130 can be omitted.

Figure 3:
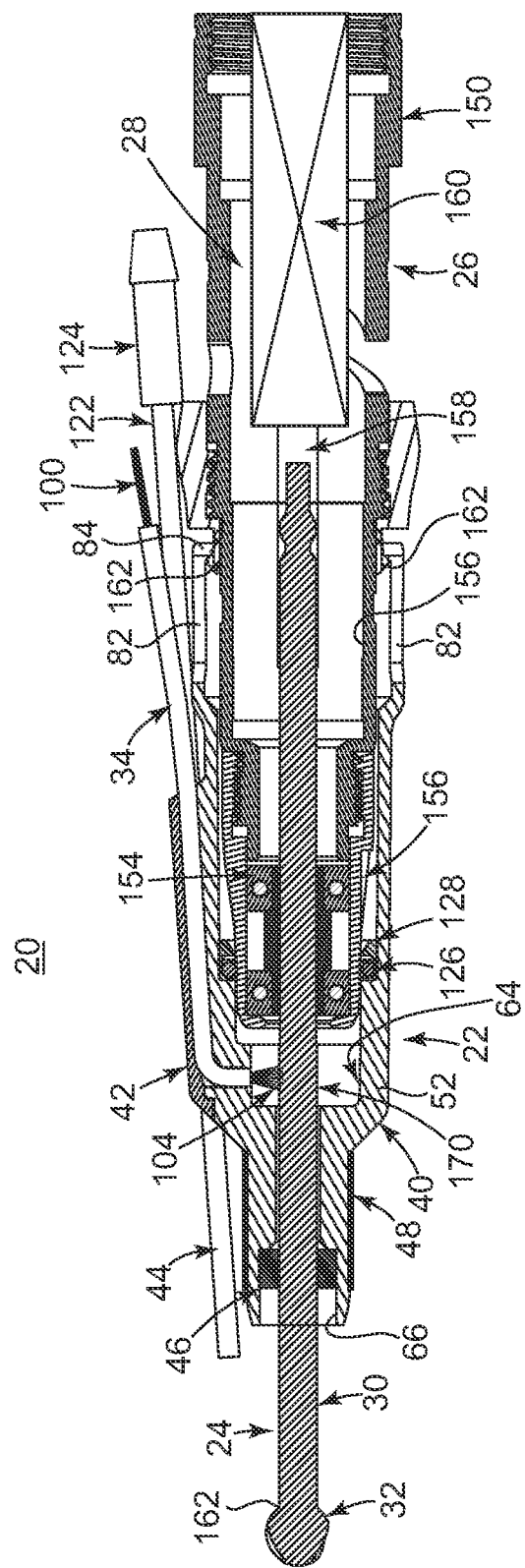
FIG. 3 is a cross-sectional view of the instrument of FIG. 1 upon final assembly.

Assembly of the guard 22 and the cutting tool 24 to the handpiece 26 is shown in FIG. 3. As a point of reference, the handpiece 26 can assume a variety of forms, and generally includes an outer housing 150. The handpiece 26 further includes additional components useful for effectuating connection of the motor assembly 28 (FIG. 1) to the tool shank 30. For example, the handpiece 26 can include an extender piece (or "nose") 152 maintaining a bearing assembly construction 154. Additional components not otherwise reflected in FIG. 3 can also be provided. Regardless, the outer housing 150 establishes or defines an internal bore 156 within which a drive member 158 of the motor assembly 28 is maintained, with the drive member 158 effectuating connection between the tool shank 30 and a motor 160 (illustrated schematically).

With the above, general construction of the handpiece 26 in mind, the guard 22 is releasably assembled to the outer housing 150 as shown. For example, in some embodiments, the outer housing 150 can include a rim 162 sized to releasably capture the latches 84 provided by the fingers 82 of the guard housing 40. With this configuration, a snap-fit assembly of the guard 22 to the handpiece 26, and in particular to the outer housing 150, is provided, with the guard 22 being released from the handpiece 26 by forcing the housing 40 distally away from the outer housing 150. With insertion or removal of the guard 22, the fingers 82 deflect, allowing the latches 84 to engage with, or release from, the rim 162. As indicated above, a wide variety of other constructions are equally applicable for effectuating releasable connection between the guard 22 and the handpiece 26.

Upon assembly of the guard 22 to the handpiece 26, the passageway 64 of the housing 40 is aligned with, or open relative to, the bore 156, thereby permitting assembly of the cutting tool 24. As a point of reference, the cutting tool 24 can assume any number of configurations known, or in the future conceived, appropriate for performing a desired surgical cutting or micro-cutting procedure. In basic terms, the cutting tip 32 is attached to, or is formed by, a distal region 162 of the tool shank 30. The cutting tip 32 can be an appropriately sized and shaped bur-type head (e.g., round bur, acorn bur, etc.) Further, while the tool shank 30 is shown as being relatively straight, in other configurations the tool shank 30 can have one or more curves, and may be externally supported by an outer tube. Regardless, the tool shank 30 and the cutting tip 32 are formed of a hard, surgically safe material, such as M2 steel (it being understood that a material of the cutting tip 32 can differ from that of the tool shank 30).

With the above arrangement, the tool shank 30 can be inserted through the leading end opening 66 of the guard housing 40, through the passageway 64, and into the bore 156 of the handpiece 26 for selective coupling with the drive member 158. As reflected in FIG. 3, upon insertion of the tool shank 30 through the intermediate segment 52, the exposed first end 104 of the wire 100 physically contacts the tool shank 30. In this regard, while portions of the tool shank 30 may be encompassed within an electrically non-conductive insulative material (as described below), a region of contact 170 of the tool shank 30 is capable of establishing an electrical coupling with the wire end 104. Thus, for example, where the cutting shank 30 is formed of a conductive metal, the region of contact 170 is exposed or not otherwise "covered" by an insulative material. With this construction, then, the exposed wire end 104 provides a low friction, low wear, sliding electrical contact against the tool shank 30 (akin to an electrical slip ring) with rotation of the cutting tool 24. As a result, a conductive pathway is established from the second end 106 of the wire 100 to the cutting tip 32 via the electrical contact between the first wire end 104 and the tool shank 30 at the region of contact 170.

As mentioned above, in some embodiments, the optional bearing member 46 engages the tool shank 30 in a manner allowing rotation of the cutting tool 24 at a location distal the handpiece 26, serving to minimize wobbling and/or vibration of the cutting tool 24 during high-speed rotation. In this regard, the collar 48, where included, provides additional support for the bearing member 46, minimizing possible creeping of the bearing member 46 along the tool shank 30 during rotation of the cutting tool 24, as well as to reinforce the housing 40 against cracking along at the leading segment 50.

Finally, as reflected in FIG. 3, upon final assembly, the optional O-ring 126 abuts against the outer housing 150 (e.g., at the extender piece 152), as maintained by the holder 128. With this relationship, the O-ring 126 dampens vibrations in the guard housing 40 during operation of the motor assembly 28.

Regardless of an exact form, the assembled surgical cutting instrument 20 is useful in performing various surgical cutting procedures as part of a surgical system that may or may not include delivery of electrical energy to a target site via the cutting tip 32. For example, FIG. 4 illustrates a surgical cutting system 200 including the instrument 20. In addition, the system 200 includes a power source 202 for powering the motor assembly 28 (referenced generally), as well as an energy source 204 electrically connected to the guard 22. The power source 202 can assume a variety of forms, and can provide a user with an ability to control powering of the motor assembly 28 (e.g., via an optional switch device 206, such as a foot switch), as well as operational parameter information. For example, in one configuration, the power source 202 is provided as part of a drill console, such as an XPS® 3000 console available from Medtronic Xomed, Inc., of Jacksonville, Fla.

The energy source 204 can also assume a wide variety of forms, and can be configured for performing a desired procedure. For example, in some embodiments, the system 200 is employed to perform evoked potential monitoring as part of a surgical cutting operation, with the energy source 204 being an evoked potential patient monitor system. The evoked potential monitor system 204 can be a nerve integrity monitoring system, such as an NIM-Response® 2.0 nerve integrity monitor system available from Medtronic Xomed, Inc., of Jacksonville, Fla. In general terms, the evoked potential monitor system 204 is adapted to indicate when an energized probe, for example the cutting tip 32, is proximate a nerve (not shown) during a surgical cutting procedure. The evoked potential monitor system 204 can include a patient interface console 208 and a patient interface box 210 through which various probes/electrodes and the guard 22 are commonly linked to the console 208. For example, the monitor system 204 can further include EMG electrodes 212a, 212b, a ground or reference electrode 214, and a stimulation return path electrode 216. The return path electrode 216 provides a return path for the stimulation current delivered by the cutting tip 32 for applications in which the delivered stimulating current is an isolated output that is not earth referenced (and therefore requires its own isolated return). The ground or reference electrode 214 provides a common reference between a patient 218 and the monitor system 204 (required to center the EMG electrode 212a, 212b signals within the input range of the recording amplifiers). The reference and return path electrodes 214, 216 can be placed in a variety of locations on the patient 218. Regardless, upon detecting or otherwise determining that the cutting tip 32 is proximate critical anatomy (e.g., a nerve) of the 218, the monitor system 204 is adapted to deliver a warning or other relevant information to the user.

As shown, the power source 202 is electrically coupled to the surgical cutting instrument 20, and in particular the motor assembly 28, via an appropriate electrical connector 230. The monitor system/energy source 204 is electrically coupled to the wiring 34 provided with the guard 22. With the one configuration of FIG. 4, the wiring 34 is connected to a port of the power source/console 202, that in turn establishes an electrical connection between the wiring and the patient interface box 210 (and thus the energy source 204) via a patch cable 232. In other configurations, the wiring 34 can be connected directly to the patient interface box 210/energy source 204. The arrangement of FIG. 4, however, can facilitate desired electrical insulation of the system 200. For example, where the cutting tool 24 is not electrically insulated, it may be possible for electrical energy applied to the cutting tool 24 (via the energy source 204) to be conducted to the motor assembly 28 and/or to the handpiece 26 due to physical contact within the handpiece 26. Under these circumstances, proper grounding of the system 200 is desired to avoid user injury and system failure, and can be accomplished by providing the power source/console 202 as a BF rated (ground floating) device, and by commonly connecting the motor assembly 28 and the wiring 34 to the BF (ground floating) console 202. Alternatively, where the cutting tool 24 is electrically insulated, the power supply console 202 can take other forms (e.g., earth grounded device), and the wiring 34 can be directly connected to the energy source 204/patient interface box 210.

During use, the cutting tip 32 is maneuvered toward a surgical target site at which surgical cutting is desired. The cutting tool 204 is then rotated at high speeds via the motor assembly 28 as powered by the power source 202. In connection with these procedures, the energy source 204 prompts delivery of a stimulating energy (e.g., a continuous, pulsed current) through the wiring 34 to the cutting tip 32 via the electrical pathway established by direct contact between the wire 100 (FIG. 2A) and the tool shank 30. The patient electrodes 212-216 provide the energy source/monitor system 204 with information indicative of a proximity of the cutting tip 32 to a nerve in response to the applied stimulating energy. For example, based upon a comparison of the applied stimulating energy with the signaled information from the patient electrode(s) 212-216, the energy source monitor system 204 can detect and/or provide the surgeon with information indicative of the energized cutting tip 32 being at or within a close distance of the nerve(s) of concern. The motor assembly 28 is simultaneously powered to rotate the cutting tip 32. Thus, simultaneous or substantially concurrent bone or tissue cutting and nerve probing functions can be performed by the system 200. Further, evoked potential monitoring can be performed via the system 200 with the motor assembly 28 being deactivated (i.e., "off" or not otherwise driving the cutting tool 24) when an indication is given that the cutting tip 32 is in close proximity to one or more nerves.

While the surgical instrument 20 has been described with the wiring 34 extending away from the guard housing 40 and the handpiece 26 for direct connection at an end thereof to an energy source, in other embodiments, the wiring 34 instead is configured for electrical connection to a corresponding feature of the handpiece 26 that in turn establishes an electrical connection to the energy source (directly or indirectly). For example, FIG. 5 is a simplified illustration of a portion of an alternative surgical instrument 234 including a guard 236 and a handpiece 238. The guard 236 is akin to the guard 22 (FIG. 2B) previously described, and generally includes a housing 240 maintaining wiring 242. A first end 244 of the wiring 242 has or forms an electrically exposed wire(s) 246 (e.g., a plurality of splayed wire strands as part of a carbon fiber wire). The wiring 242 extends along a portion of an exterior of the housing 240, terminating at a second end 248. The second end 248 is, or is attached to, an electrical contact element 250. As shown, the contact element 250 projects through a wall thickness of the housing 240, and is electrically exposed within an interior (i.e., passageway) of the housing 240. The electrical contact element 250 can be formed from a variety of materials (e.g., any electrically conductive metal such as brass, stainless steel, gold plated material, etc.), and can have varying forms (e.g., can be a spring loaded body). Regardless, the first end 244 of the wiring 242 is electrically connected to the contact element 250.

As with previous embodiments, the guard 236 and the handpiece 238 are constructed such that the housing 240 is releasably attachable to the handpiece 238, such as by being placed over a distal section 252 of the handpiece 238. To this end, the handpiece 238 is akin to the handpiece 26 (FIG. 1) previously described, and further includes a conductive ring 254 and a wire 256. The conductive ring 254 is exteriorly exposed relative to the distal section 252, and is electrically connected to the wire 256. The wire 256, in turn, extends proximally along the handpiece housing 258, and can terminate at, or extend along, cabling (not shown) connectable to an energy source (either directly or via a power source that establishes an auxiliary connection to the energy source as described above with respect to FIG. 4). Regardless, the guard housing 236 and the handpiece distal section 252 are sized and shaped such that upon final assembly of the guard 236 to or over the handpiece 238, the contact element 250 contacts, or is in electrical communication with, the conductive ring 254. Optionally, non-conductive rings 260 can be provided at opposite sides of the conductive ring 254 to electrically insulate the conductive ring 254.

With the above construction, upon final assembly, an electrical pathway is established between the handpiece wire 256 (and thus any energy source connected to the wire 256) and the guard wiring first end 244 via the contact between the contact element 250 and the conductive ring 254. As a result, a single cabling can be employed with the instrument 234 for connection to one or more power or energy sources.

FIG. 6 is a simplified view of a portion of another alternative surgical instrument 262 including a guard 264 and a handpiece 266. The instrument 262 is akin to the instrument 234 (FIG. 5) previously described, with the guard 264 including a housing 268 maintaining wiring 270. The wiring 270 is electrically exposed at an end (hidden in the view of FIG. 6) disposed within an interior or passageway of the housing 268. A second end 272 of the wiring 270 is connected to or forms an electrical connector 274 (e.g., an electrical pin) adapted to be electrically coupled to an electrical receptacle 276 provided with the handpiece 266 (e.g., on an exterior of a housing 278 of the handpiece 266). The receptacle 276 is electrically connected to a wire (not shown) that in turn is connected to, or provided as part of, cabling (not shown). Assembly of the guard 264 to the handpiece 266 includes connecting the connector 274 with the receptacle 276, thereby establishing electrical communication between the guard wiring 270 that in turn is connected to the separate energy source (not shown) via the cabling.

Figure 7:
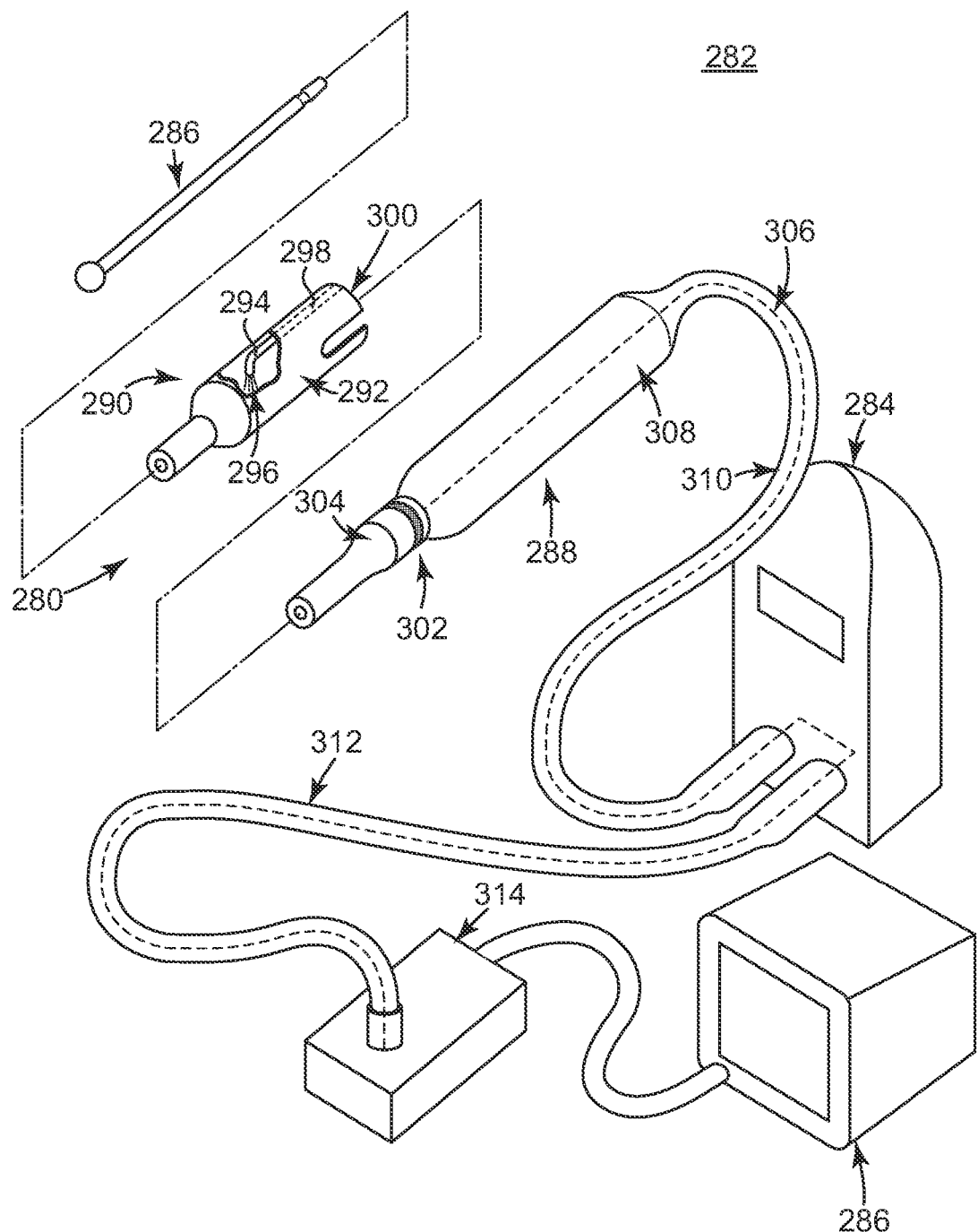
FIG. 7 is a simplified perspective view of another surgical cutting system in accordance with aspects of the present disclosure.

Yet another alternative surgical instrument 280 is shown in FIG. 7 as part of a system 282 including a power source 284 and an energy source 286. The instrument 280 has a cutting tool 286, a handpiece 288 (maintaining a motor assembly (not shown)), and a guard 290. The guard 290 is akin to any of the embodiments previously described, and generally includes a housing 292 and wiring 294. A first end 296 of the wiring 294 is electrically exposed within an interior or passageway of the housing 292 for contacting, and establishing an electrical pathway with, the cutting tool 286 as previously described. A second end 298 of the wiring 294 is, or is connected to, a contact conductor 300 carried at an interior of the housing 292.

The handpiece 288 can have any of the forms previously described, and includes a conductive ring 302 along a distal portion 304 thereof. The conductive ring 302 is electrically connected to a wire 306 carried within a housing 308 of the handpiece 288. The wire 306, in turn, extends along cabling 310 that further includes one or more other wires, such as wires connected to the motor assembly (not shown).

With the above construction, assembly of the system 282 includes assembling the guard 290 to the handpiece 288, followed by connection of the cutting tool 286 to the handpiece 288 (and the motor assembly (not shown) carried thereby) via insertion of a shank of the cutting tool 286 through the guard 290. The cabling 310 is connected to the power source 284 (e.g., a drill console), establishing an electrical connection between the power source 284 and the motor assembly. A patch cable 312 connects the power source 284 with the energy source 286, for example via an intermediate patient interface box 314. Regardless, electrical communication is established along a pathway from the energy source 286 to the first end 296 of the guard wiring 294, and thus the cutting tool 286. The so-configured system 282 can then operate as previously described.

As described above with reference to FIG. 4, a stimulating energy is applied onto the cutting tool 24. The surgical cutting instrument of the present disclosure can incorporate or make use of a "standard" cutting tool configuration in which the cutting tip 32 and the tool shank 30 are commonly formed of a metallic, electrically conductive material (e.g., M2 steel). Use of a BF (ground floating) power supply can promote acceptable operation of the system 200 with non-insulated cutting tools 24. In other embodiments, however, the cutting tool 24 can be configured to incorporate non-conductive features so as to electrically isolate the cutting tool 24 from the handpiece 26.

Figure 8:
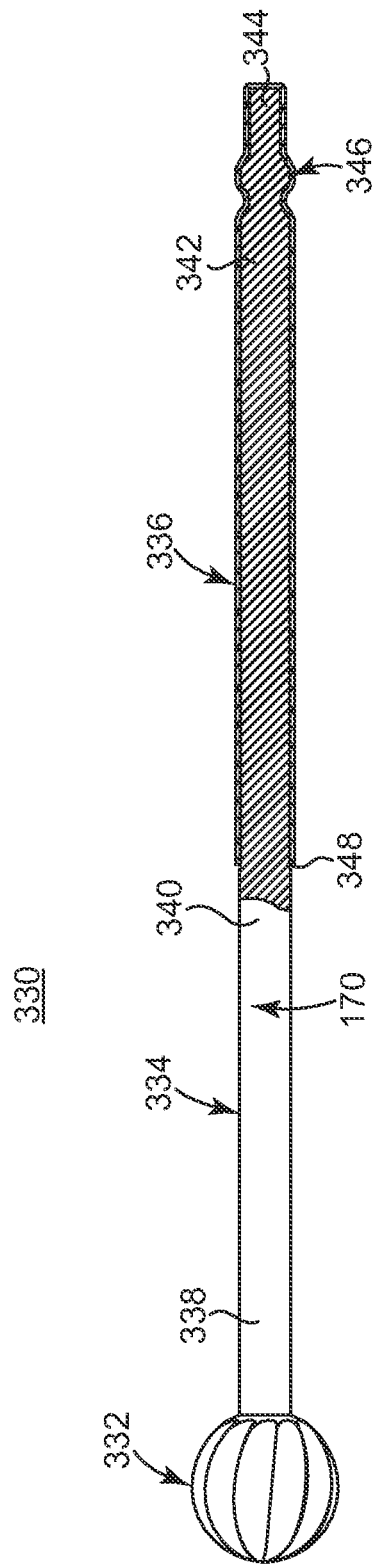
FIG. 8 is a side view, with portions shown in cross-section, of a cutting tool useful with the instrument of FIG. 1.

For example, FIG. 8 illustrates an alternative cutting tool 330 useful with the cutting instrument 20 (FIG. 1). The cutting tool 330 includes a cutting tip 332, a tool shank 334, and an electrically non-conductive, insulative material 336. In general terms, the cutting tip 332 is attached to the tool shank 344, and the insulative material 336 is applied over a portion of the tool shank 334, serving to electrically insulate that portion.

The tool shank 334 defines a distal segment 338, an intermediate segment 340, and a proximal segment 342 terminating at a proximal end 344. The distal segment 338 is attached to or otherwise forms the cutting tip 332. As a point of reference, the cutting tip 332 can assume either of the forms previous described, and for example is a bur-type cutting tip. Regardless, the proximal segment 342 is configured for attachment to the drive member 158 (FIG. 3) associated with the motor assembly 28 (FIG. 3). Thus, for example, the proximal segment 342 can form an engagement feature 346 sized and shaped to releasably interface with a corresponding feature of the drive member 158. The engagement feature 346 can assume a variety of other forms apart from that specifically shown.

The insulative material 336 is applied over an exterior of the tool shank 334 along the proximal segment 342 and a portion of the intermediate segment 340. In this regard, the insulative material 336 encompasses or covers the proximal end 344. A length or extension of the insulative material 336 (i.e., relative to a longitudinal length of the tool shank 334) is selected in accordance with various features of the cutting instrument 20. For example, and with reference to FIG. 3, a longitudinal distance between the drive member 158 and the first wire end 104 upon assembly to the guard 22 to the handpiece 26 is known. Thus, a location of the region of contact 170 relative to a length of the tool shank 30 (and thus relative to the tool shank 334) is also known. With this in mind, then, the insulative material 336 terminates at an end 348 that is proximal the region of contact 170 (referenced generally in FIG. 8). With this construction, then, upon assembly of the cutting tool 330 to the handpiece 26, the region of contact 170 is electrically "exposed" for establishing the desired electrical coupling with the first wire end 104.

The insulative material 336 can assume a variety of forms, and can be applied to the tool shank 334 in different manners. In some configurations, the insulative material 336 is an electrically non-conductive polyester material (e.g., tubing) that is heat shrunk onto the tool shank 334.

Figure 9:
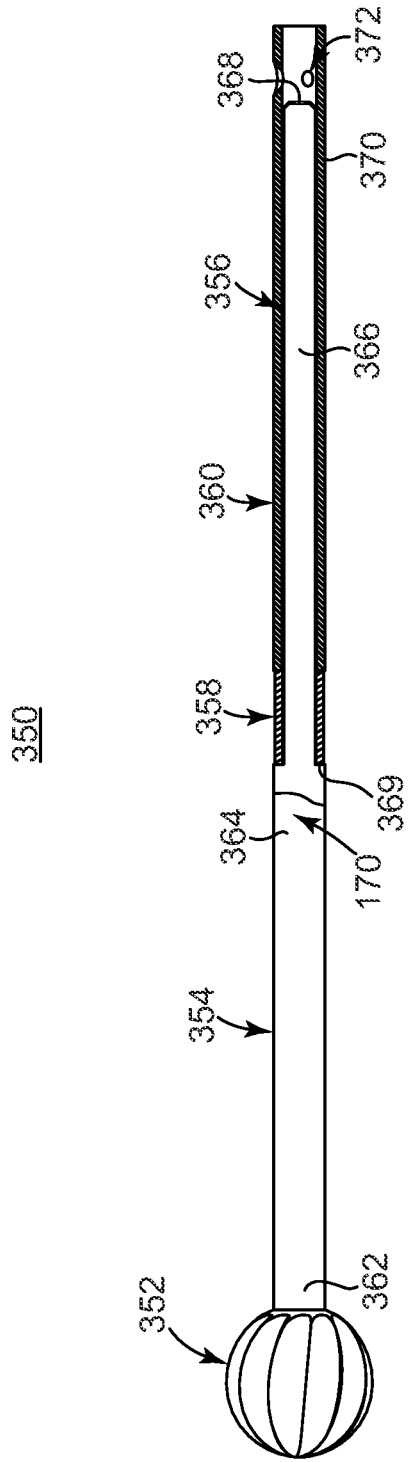
FIG. 9 is side view, with portions shown in cross-section, of a cutting tool useful with the instrument of FIG. 1.

Another cutting tool 350 useful with the surgical instrument 20 (FIG. 1) is shown in FIG. 9. The cutting tool 350 includes a cutting tip 352, a tool shank 354, an electrically non-conductive insulative material 356, a spacer 358, and a coupling member 360. The tool shank 354 maintains the cutting tip 352, and the insulative material 356 is applied over a portion of the tool shank 354. The coupling member 360 is assembled over the tool shank 354 in a region of the insulative material 356. Finally, the spacer 358 maintains an electrical isolation between the tool shank 354 and the coupling member 360.

The tool shank 354 defines a distal segment 362, an intermediate segment 364, and a proximal segment 366 terminating at a proximal end 368. The cutting tip 352 is attached to or formed by the distal segment 362. As with previous configurations, the cutting tip 352 and the tool shank 354 are formed of a hardened, electrically conductive material, such as M2 steel. Relative to a length of the tool shank 354, the intermediate segment 364 forms a shoulder 369. The shoulder 369 represents an increase in diameter of the tool shank 354 from the proximal segment 366 to the distal segment 362. Commensurate with previously-described configurations, the shoulder 369 is positioned proximal the region of contact 170. That is to say, the shoulder 369 is formed to be proximal the location at which the first wire end 104 (FIG. 3) contacts the tool shank 354 upon assembly to the handpiece 26 (FIG. 3).

The insulative material 356 is applied over an exterior of the tool shank 354, extending along an entirety of the proximal segment 366 and a portion of the intermediate segment 364 to the shoulder 369. The insulative material 356 can assume a variety of forms, and in some configurations is a polyester film or material (e.g., in tubular form) heat shrunk onto the tool shank 354. The spacer 358 is formed of an electrically non-conductive material (e.g., plastic), and is configured for assembly over the tool shank 354. For example, in some embodiments, the spacer 358 is a ring. With these configurations, an inner diameter of the ring is commensurate with a diameter of the tool shank 354 proximal the shoulder 369. As such, the spacer 358 can be coaxially assembled over the tool shank 354 by sliding the spacer 358 from the proximal end 368 to a point of contact with the shoulder 369. Further, the spacer 358 has an outer diameter or thickness commensurate with an outer diameter of the tool shank 354 distal the shoulder 369.

The coupling member 360 is formed of a relatively rigid material appropriate for maintaining connection with the drive member 158 (FIG. 3) during high-speed rotation. In this regard, a proximal region 370 of the coupling member 360 forms or includes an engagement feature 372 adapted to releasably couple with a corresponding feature of the drive member 158. With some configurations, the coupling member 360 is a stainless steel tube, although other constructions are also envisioned. Where provided as tubing, an inner diameter of the coupling member 360 is commensurate with diameter of the tool shank 354 proximal the shoulder 369, whereas an outer diameter of the coupling member 360 is commensurate with a diameter of the tool shank 354 distal the shoulder 369.

Assembly of the cutting tool 350 can include providing or forming the tool shank 354 as shown. The insulative material 356 is applied over the proximal segment 366 and a portion of the intermediate segment 364 to the shoulder 369 (e.g., heat shrunk onto the tool shank 354). The spacer 358 and the coupling member 360 are then installed over the tool shank 354 as shown. The cutting tool 350 can then be subjected to heat, causing the insulative material 356 to melt. Upon cooling, the insulative material 356 re-solidifies and effectuates a bond between the tool shank 354 and the coupling member 360. Regardless, the coupling member 360 is electrically isolated from the region of contact 170 (and all other portions of the tool shank 354 distal the shoulder 369) via the insulative material 356 and the spacer 358. In this regard, the cutting tool 350 has a robust configuration, capable of maintaining durability during high speed rotation, while exhibiting a requisite dielectric strength.

Figure 10:
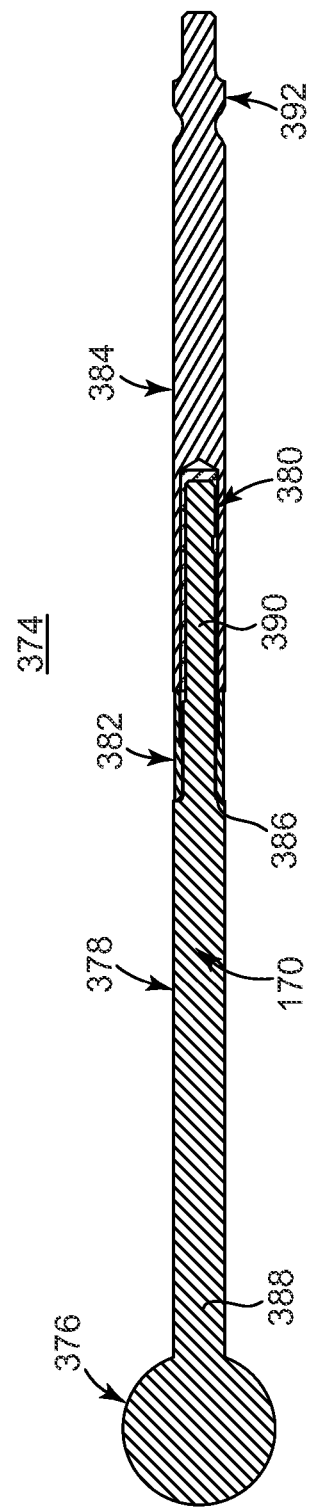
FIG. 10 is side view, with portions shown in cross-section, of a cutting tool useful with the instrument of FIG. 1.

Another configuration of a cutting tool 374 useful with the surgical cutting instrument (FIG. 1) is shown in FIG. 10. The cutting tool 374 includes a cutting tip 376, a tool shank 378, a dielectric layer 380, a spacer 382, and a coupling member 384. The tool shank 378 is akin to the tool shank 354 (FIG. 9) previously described, and forms a shoulder 386 intermediate a distal segment 388 and a proximal segment 390 thereof. Once again, the shoulder 386 reflects an increase in diameter of the tool shank 378 from the proximal segment 390 to the distal segment 388, and is located proximal the region of contact 170 (referenced generally). The spacer 382 is formed of an electrically non-conductive material, and is assembled over the tool shank 378 so as to abut, and extend proximally from, the shoulder 386. The coupling member 384 is also assembled over the proximal segment 390 of the tool shank 378, and is configured for releasable connection to the drive member 158 (FIG. 3), for example via an engagement feature 392. In addition, the coupling member 384 is formed of a hardened material, such as stainless steel, capable of maintaining its integrity during high-speed rotation. Finally, the coupling member 384 is affixed to the tool shank 378 via the dielectric layer 380. More particularly, the dielectric layer 380 exhibits adhesive properties in bonding the coupling member 384 to the tool shank 378. Further, the dielectric layer 336 along with the spacer 382 electrically insulates the coupling member 384 from the tool shank 378.

Figure 11:
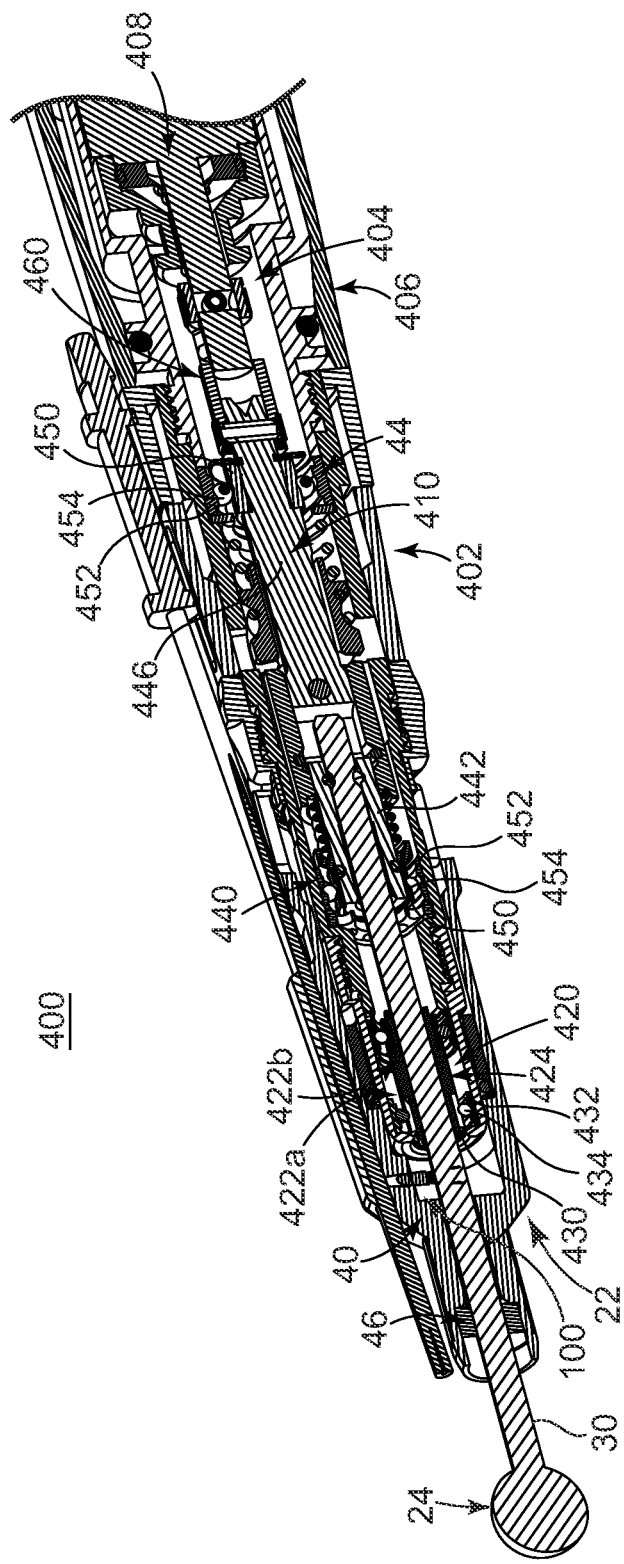
FIG. 11 is a perspective, cross-sectional view of another surgical instrument in accordance with aspects of the present disclosure.

While the cutting tools 330 (FIG. 8), 350 (FIG. 9), and 374 have been described as providing electrical insulation relative to the handpiece 26 (FIG. 3) upon final assembly, in other embodiments, the cutting tool can have a conventional configuration in which an electrically non-conductive feature is absent. With these configurations, it may be useful to incorporate one or more other features into the handpiece 26 to promote electrical isolation from the cutting tool. For example, a surgical cutting instrument 400 in accordance with some aspects of the present disclosure is provided in FIG. 11. The instrument 400 includes the guard 22 and the cutting tool 24 (in non-insulated form) as previously described. In addition, the instrument 400 includes a handpiece 402 maintaining a motor assembly 404. The handpiece 402 includes an outer housing 406 along with other components described below. The motor assembly 404 generally includes a motor 408 connected to a driving member 410. The cutting tool 24 and the driving member 410 are configured to effectuate a releasable coupling therebetween via appropriate engagement features. As described below, the handpiece 402 is configured to electrically isolate the cutting tool 24 (when otherwise energized via the wire 100) from the outer housing 406.

For example, in some configurations, the handpiece 402 includes a bearing assembly construction 420 consisting of, for example, one or more bearing assemblies 422a, 422b and a sleeve 424. The bearing assemblies 422a, 422b can assume a variety of forms (e.g., ball bearing assemblies) formed of electrically conductive or non-conductive materials. Regardless, the bearing assemblies 422a, 422b rotatably maintain the sleeve 424 that otherwise frictionally receives and supports the tool shank 30 upon assembly to the handpiece 402. In this regard, the sleeve 424 is formed of a durable, electrically non-conductive material such as ceramic. The driving member 410 is also formed of a durable, electrically non-conductive material such as ceramic.

With the above configuration, upon assembly of the cutting tool 24 to the handpiece 402, the tool shank 30 is in direct contact with only the driving member 410 and the sleeve 424 of the handpiece 402. In addition, the cutting tool 24 may also be in direct physical contact with one or more features of the guard 22, such as the optional bearing member 46. Under these circumstances, the instrument 400 electrically isolates the non-insulated cutting tool 24 from the outer housing 406. More particularly, the driving member 410 and the sleeve 424 are formed of electrically non-conductive material, such that electrical energy is not transmitted to other components of the handpiece 402 via the driving member 410 or the sleeve 424.

Further, the guard housing 40 is formed of an electrically non-conductive material, such that electrical energy is not transmitted to a region of interface or contact between the guard housing 40 and the handpiece 402. During use, then, a stimulating electrical energy can safely be applied to the tool shank 30 via the wire 100 while the user is grasping the outer housing 406.

Alternatively, or in addition, other components of the handpiece 402 can be configured to effectuate electrical isolation of the outer housing 406 from the cutting tool 24. For example, and as previously described, the bearing assembly construction 420 can include the bearing assemblies 422a, 422b. More particularly, in some configurations, the bearing assemblies 422a, 422b each consist of an inner race 430, an outer race 432, and a plurality of ball bearings 434 captured therebetween. The races 430, 432 can be formed of any desired material that may or may not be electrically conductive. However, the spheres 434 are formed of a hardened, electrically non-conductive material, such as ceramic.

In addition to the bearing assembly construction 420, the handpiece 402 can further include an intermediate bearing assembly 440 positioned adjacent a distal end 442 of the driving member 410 for rotatably supporting the cutting tool 24/driving member 410 interface. Further, a proximal bearing assembly 444 can be provided adjacent a proximal end 446 of the driving member 410 for supporting the driving member 410/motor 408 interface. The bearing assemblies 440, 444 are similar to the bearing assemblies 422a, 422b previously described, and each include an inner race 450, an outer race 452, and a plurality of ball bearings 454 captured therebetween. Once again, the races 450, 452 can be formed of any desired material that is conductive or electrically non-conductive. The ball bearings 454, however, are formed of a hardened, electrically non-conductive material such as ceramic. Notably, while the handpiece 402 can include additional features or components that exteriorly support the bearing assemblies 422a, 422b, 440, 444, these structures are not in direct physical contact with the cutting tool 24 or the driving member 410. That is to say, apart from the guard 22, the only electrical pathways between the outer housing 406 and the cutting tool 24, and between the outer housing 406 and the driving member 410, include the bearing assembly 422a, 422b, 440, 444. Due to the electrically non-conductive nature of the corresponding ball bearings 434, 454, electrical energy is not transmitted through these pathways.

Finally, a coupling 460 is provided that connects the driving member 410 with the motor 408. With this construction, at least one of the coupling 460 or the driving member 410 is formed of an electrically non-conductive material such as ceramic, thereby isolating the motor 408 from the tool shank 30.

The electrically non-conductive ball bearing 434, 454 electrically isolate the non-insulated cutting tool 24 from the outer housing 406. Further, the electrically non-conductive housing 40 electrically isolates the guard 22 from the outer housing 406. Finally, the electrically non-conductive coupling 460 and/or the driving member 410 electrically isolates the non-insulated cutting tool 24 from the motor 408. With this construction, then, the cutting tool 24 is electrically isolated from the outer housing 406 and the motor 408.

Although specific embodiments have been illustrated and described herein, it will be appreciated by those of ordinary skill in the art that a variety of alternate/equivalent implantations may be substituted for the specific embodiments shown and described without departing from the spirit and scope of the present disclosure. This application is intended to cover any adaptations or variations of the specific embodiments discussed herein. Therefore, it is intended that this disclosure be limited only by the claims and the equivalence thereof.

What is claimed is:

1. A removable guard for use with a surgical cutting instrument, the guard comprising:
   a guard housing forming a homogenous structure defining a leading end, a trailing end, a longitudinal passageway extending therebetween, and an aperture extending between an exterior of the guard housing and the passageway, wherein the passageway is open at a trailing end opening sized and shaped to releasably receive a distal end of an outer housing of a surgical cutting instrument handpiece, and is open at a leading end opening sized to releasably receive a cutting tool shank, and further wherein the guard housing is positioned over the distal end of the outer housing; and
   wiring coupled to the guard housing, the wiring including:
      an electrically conductive carbon fiber wire extending through the aperture and defining and extending continuously between opposing, first and second ends, wherein the first end is positioned within the passageway and the second end is positioned exterior of the aperture, and wherein the first end of the wire includes a plurality of wire strands splayed apart relative to one another; and
   electrically non-conductive insulative material covering at least a majority of the wire apart from the first end such that the first end of the wire is exposed within the passageway for establishing an electrical connection with a cutting tool shank disposed within the passageway.

2. The guard of claim 1, wherein the passageway defines a central axis and a minimum radius, and further wherein the wire is positioned such that the first end projects toward the central axis and terminates at a point within the minimum radius.

3. The guard of claim 2, wherein the minimum radius is commensurate with a radius of a cutting tool shank.

4. The guard of claim 1, further comprising:
   a cover attached to the exterior of the guard housing, wherein a segment of the wiring is enclosed between the cover and the guard housing.

5. The guard of claim 1, wherein the wiring includes a first segment extending from the first end and a second segment extending from the second end, and further wherein the first segment is affixed to the guard housing and the second segment is movable relative to the guard housing.

6. The guard of claim 1, wherein the guard housing is formed of an electrically non-conductive material.

7. The guard of claim 1, wherein the guard housing forms a plurality of deflectable fingers combining to define the trailing end opening and configured to releasably engage an instrument handpiece.

8. The guard of claim 1, further comprising:
   a bearing member disposed within the passageway adjacent the leading end opening for rotatably supporting a cutting tool shank.

9. The guard of claim 1, further comprising:
   a collar assembled to an exterior of the guard housing in a region of the bearing member.

10. The guard of claim 9, wherein the guard housing defines a leading segment extending from the leading end and a trailing segment extending from the trailing end, the leading segment having a diameter less than a diameter of the trailing segment, and further wherein the collar is assembled to the leading segment.

11. The guard of claim 1, further comprising:
    irrigation tubing coupled to the guard housing.

12. The guard of claim 11, wherein the irrigation tubing extends external to the passageway and defines a distal end and a proximal end, and further wherein the distal end is positioned distal the leading end of the guard housing.

13. A surgical cutting system comprising:
a cutting tool including a cutting tip and a tool shank extending proximally from the cutting tip;
a motor assembly including a motor rotatably driving a drive mechanism;
a handpiece including an outer housing defining a distal end, the handpiece coupled to the motor assembly and configured to facilitate selective connection of the tool shank with the drive mechanism within a bore defined by the handpiece such that the tool shank extends from the distal end of the outer housing; and
a guard comprising:
a guard housing formed of a homogenous structure and defining a leading end, a trailing end, a longitudinal passageway extending therebetween, and an aperture extending between an exterior of the guard housing and the passageway, wherein the trailing end is configured for releasable attachment to the handpiece via a trailing end opening of the passageway, and further wherein the guard housing is positioned over the distal end of the outer housing and the leading end is configured to permit selective placement of the tool shank within the passageway via a leading end opening,
wiring coupled to the guard housing, the wiring including:
an electrically conductive carbon fiber wire extending through the aperture and extending continuously between opposing, first and second ends, wherein the first end is positioned within the passageway and the second end is position exterior of the aperture, and wherein the first end of the wire includes a plurality of wire strands splayed apart relative to one another; and
electrically non-conductive insulative material encompassing at least a majority of the wire apart from the first end such that the first end is exposed within the passageway;
wherein upon final assembly, the handpiece is disposed within the passageway, the tool shank extends through the passageway and is connected to the drive mechanism, and the first end of the wire contacts the tool shank.

14. The system of claim 13, further comprising:
an evoked potential monitoring system having an energy source selectively electrically coupled to the second end of the wire for applying a stimulating energy to the cutting tip via the wire and the contact between the wire first end and the tool shank.

15. The system of claim 13, wherein the guard is configured such that upon final assembly, continuous contact between the first end of the wire and the tool shank is maintained with rotation of the tool shank by the motor assembly.

16. The system of claim 13, wherein the guard is configured such that upon final assembly, the first end of the wire contacts the tool shank distal the handpiece.

17. The system of claim 13, wherein the housing is formed of an electrically non-conductive material.

18. The system of claim 13, wherein the guard housing is configured to permit insertion and removal of the tool shank via the passageway, and further wherein the guard is configured such that the first end of the wire contacts the tool shank with insertion of the tool shank through the passageway.

19. The system of claim 13, wherein the guard further comprises:
a bearing member disposed within the passageway adjacent the leading end opening for rotatably supporting the cutting tool shank.

20. The system of claim 19, wherein the guard further comprises:
a collar assembled to an exterior of the guard housing adjacent the leading end and adapted to support an interface between the tool shank and the bearing member.

21. The system of claim 13, wherein the guard further comprises:
a seal member assembled within the passageway adjacent the leading end, wherein the seal member defines an aperture sized to selectively receive the tool shank, the seal member establishing a fluid-tight seal against the tool shank upon final assembly.

22. The system of claim 13, wherein the tool shank defines a proximal segment, the cutting tool further comprising:
a non-conductive material applied over an exterior of the proximal segment; and
a connector piece configured for connection to the drive mechanism and assembled over the non-conductive material.

23. The system of claim 22, wherein the tool shank further defines an intermediate segment extending distally from the proximal segment, the intermediate segment forming a shoulder having a diameter greater than a diameter of the proximal segment, and further wherein the connector piece terminates at an end proximal the shoulder, the cutting tool further comprising:
a non-conductive spacer assembled over the tool shank between the end of the connector piece and the shoulder.

24. The system of claim 13, wherein the handpiece includes:
the outer housing adapted to be grasped by a user; and
a bearing sleeve adapted to support the tool shank upon final assembly, the bearing sleeve formed of an electrically non-conductive material;
wherein the drive mechanism is adapted to receive and contact the tool shank and is formed of an electrically non-conductive material;
and further wherein upon final assembly, the bearing sleeve and the drive mechanism electrically isolate the outer housing and an electrical ground of the motor from the tool shank.

25. The system of claim 13, wherein the handpiece includes:
the outer housing adapted to be grasped by a user;
a first ball bearing assembly rotatably supporting the tool shank upon final assembly; and
a second ball bearing assembly rotatably supporting the drive mechanism;
wherein the ball bearing assemblies each include an inner race, an outer race, and a plurality of ball bearings movably captured between the races, the ball bearings being formed of an electrically non-conductive material to electrically isolate the outer housing and an electrical ground of the motor from the tool shank.

* * * * *

UNITED STATES PATENT AND TRADEMARK OFFICE
CERTIFICATE OF CORRECTION

| | |
|---|---|
| PATENT NO. | : 8,945,164 B2 |
| APPLICATION NO. | : 11/760530 |
| DATED | : February 3, 2015 |
| INVENTOR(S) | : William Charles Brunnett et al. |

It is certified that error appears in the above-identified patent and that said Letters Patent is hereby corrected as shown below:

In the claims:

Claim 13; column 17, line 35-36 delete "and the second end is position exterior of the aperture," and insert in place thereof --and the second end is positioned exterior of the aperture,--

Signed and Sealed this
Fourth Day of August, 2015

Michelle K. Lee
*Director of the United States Patent and Trademark Office*